US006767328B2

(12) United States Patent
Kulik (10) Patent No.: US 6,767,328 B2
(45) Date of Patent: Jul. 27, 2004

(54) METHOD AND APPARATUS FOR DETERMINING BLOOD PRESSURE USING PRESSURE PULSE DUTY CYCLE

(75) Inventor: Robert Stanley Kulik, Tampa, FL (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 88 days.

(21) Appl. No.: 10/064,622

(22) Filed: Jul. 31, 2002

(65) Prior Publication Data

US 2004/0024323 A1 Feb. 5, 2004

(51) Int. Cl.$^7$ .................................................. A61B 5/00
(52) U.S. Cl. ...................................... 600/494; 600/495
(58) Field of Search .............................. 600/485, 490, 600/493–6, 500

(56) References Cited

U.S. PATENT DOCUMENTS

| | | | |
|---|---|---|---|
| 4,349,034 A | 9/1982 | Ramsey, III | 128/681 |
| 4,360,029 A | 11/1982 | Ramsey, III | 128/681 |
| 4,543,962 A | 10/1985 | Medero et al. | 128/682 |
| 4,638,810 A | 1/1987 | Ramsey, III et al. | 128/681 |
| 4,889,133 A | 12/1989 | Nelson et al. | 128/681 |
| 4,922,918 A * | 5/1990 | Ruiter | 600/494 |
| 4,949,710 A | 8/1990 | Dorsett et al. | 128/680 |
| 4,958,636 A | 9/1990 | Blandino et al. | 128/630 |
| 5,054,494 A * | 10/1991 | Lazzaro et al. | 600/490 |
| 5,170,795 A | 12/1992 | Ramsey, III et al. | 128/682 |
| 5,590,662 A | 1/1997 | Hersh et al. | 128/681 |
| 5,606,977 A | 3/1997 | Ramsey, III et al. | 128/680 |
| 6,358,213 B1 | 3/2002 | Friedman et al. | 600/493 |
| 6,440,080 B1 * | 8/2002 | Booth et al. | 600/494 |

OTHER PUBLICATIONS

"Algorithms—Peakfitting, Levenber–Marquardt Method," found at http://www.galactic.com/algorithms/ cf _levenberg.htm.
"The History of Blood Pressure Monitoring," found at http://www.healthperfect.co.uk/Index/dphistry.htm.
Maynard Ramsey, III, MD, PhD; "Blood Pressure Monitoring: Automated Oscillometric Devices," Knowing Your Monitoring Equipment; Jun. 1990; pp. 56–67.
"Levenber–Marquardt Method," found at http://www-fp.mcs.anl.gov/otc/Guide/OptWEb/continuous/unconstrained/nonlinear/section.
Paul Davis; "Levenber–Marquart Methods and Nonlinear Estication," SIAM News, vol. 26; No. 6, Oct. 1993; found at http://www.siam.org/siamnews/mtc/mtc1093.htm.
Alan Miller; "Scientific Computing FAQ: Levenber–Marquardt algorithm," found at http://www.mathcom.com/corpdir/techinfo.mdir/scifaq/q230.2.1htm.
Maynard Ramsey III2; "Noninvasive Automatic Determination of Mean Arterial Pressure," Medical & Biological Engineering & Computing; Jan. 1979; vol. 17; pp. 11–18.
GB 0317972.8 Search Report.

* cited by examiner

Primary Examiner—Robert L. Nasser
(74) Attorney, Agent, or Firm—Cantor Colburn LLP (57) ABSTRACT

A method of processing oscillometric blood pressure pulse data taken from a subject is disclosed. In an exemplary embodiment, the method includes determining a pressure pulse period of a cardiac cycle of the subject and identifying a duration of a pressure pulse detected within the pressure pulse period. Then, a duty cycle of the pressure pulse is calculated with respect to the pressure pulse period, wherein the calculated duty cycle is used to determine selected blood pressure parameters.

26 Claims, 6 Drawing Sheets

METHOD AND APPARATUS FOR DETERMINING BLOOD PRESSURE USING PRESSURE PULSE DUTY CYCLE

BACKGROUND OF INVENTION

The present disclosure relates generally to non-invasive blood pressure monitoring and, more particularly, to a method and apparatus for determining blood pressure using pressure pulse duty cycle.

Since 1733, when the Reverend Stephen Hales first inserted a long, upright glass tube into the artery of a horse, the direct and invasive measurement of blood pressure remains the most accurate method for obtaining a blood pressure measurement. To obtain such accurate measurements, a catheter is inserted surgically a patient's artery and guided to the measurement site. However, due to the risk of infection and blood loss (as well as for patient comfort and convenience), non-invasive measurements are most commonly used.

Of the various non-invasive blood pressure measurement techniques in existence today, the most common is the auscultatory technique, based on the ability of the human ear to detect and distinguish sounds. In 1905, Korotkoff first described these auscultatory (i.e., characteristic) sounds that became the foundation for the auscultatory technique. In this technique, an air-filled cuff is wrapped around a patient's upper arm and is then inflated to occlude the brachial artery. As the cuff is allowed to deflate, a stethoscope is placed over the patient's brachial artery (distal to the cuff). The clinician uses the stethoscope to listen for the Korotkoff sounds as the cuff deflates. Upon gradual release of the constricted pressure, the beginning of blood flow may be heard. At that time, the pressure reading on a gauge (in millimeters of mercury) is noted, and is referred to as systolic pressure. The pressure is then further released until the sounds of flow again cease, at which time the pressure reading is once again noted. This reading is referred to as diastolic pressure.

One disadvantage of the sound dependent, auscultatory technique stems from the fact that some patients may exhibit muted sounds as a result of a condition such as hypotension (low blood pressure), for example, thus making the measurement difficult to detect. In addition, there is the possibility of measurement error due to differences in hearing acuity and measurement technique from clinician to clinician. Further, unqualified or inexperienced personnel may be more susceptible to outside noise, interference, or an inconsistent assessment of Korotkoff sounds. In an attempt to increase reproducibility, some automated devices have even replaced the human ear with a microphone.

Another existing non-invasive blood pressure measurement technique is the "oscillometric" method, which refers to any measurement of small pressure oscillations in an occlusive cuff caused by the arterial pressure pulse. The oscillometric method, like the auscultatory method, uses an occlusive cuff applied around the upper arm. However, instead of using microphones or stethoscopes to listen for characteristic sounds, oscillometric devices use pressure signal pulses picked up by the cuff to determine blood pressure. These pressure signal pulses are transmitted to the cuff by the pulsatile blood flow through the brachial artery. The signals are analyzed to determine a measure mean arterial pressure (MAP), identified as the point of maximum pulse amplitude. From this measurement, systolic and diastolic blood pressures are estimated.

Fundamentally, the amplitude approach to identifying MAP and estimating systolic and diastolic pressures appeals to the nonlinear relationship between the artery cross sectional area and the transmural pressure (the difference in pressures inside and outside the artery), primarily due to the material properties of the artery wall.

However, there are several other factors that can modify the amplitude of the pulse detected by the monitoring device including, but not limited to, changes in arterial compliance, material properties of other tissues in the arm, cuff material and wrap, and pneumatic system characteristics. Accordingly, it is desirable to be able to implement an alternative method of oscillometric measurement that avoids the complexities of measuring pulse amplitudes.

SUMMARY OF INVENTION

The above discussed and other drawbacks and deficiencies of the prior art are overcome or alleviated by a method of processing oscillometric blood pressure pulse data taken from a subject. In an exemplary embodiment, the method includes determining a pressure pulse period of a cardiac cycle of the subject and identifying a duration of a pressure pulse detected within the pressure pulse period. Then, a duty cycle of the pressure pulse is calculated with respect to the pressure pulse period, wherein the calculated duty cycle is used to determine selected blood pressure parameters.

In another aspect, a method of measuring the blood pressure of a subject includes inflating a cuff placed over an arm of the subject, thereby applying a plurality of pressure levels thereto. At each pressure level, obtaining pulse pressure data caused by blood pressure pulses within the arm of the subject is obtained and, from the pulse pressure data, a duty cycle for a pressure pulse period is calculated. The duty cycle is then used to determine selected blood pressure parameters.

In still a further aspect, an apparatus for obtaining the blood pressure of a subject includes an inflatable and deflatable pressure cuff for placement around an arm of the subject. An inflating apparatus is used for inflating and pressurizing said pressure cuff, while a deflating apparatus selectively relieves pressure from the cuff. In addition, a pressure sensing device is coupled to the cuff for sensing pulse pressure data caused by blood pressure pulses within the arm of the subject. A microprocessor processes the pulse pressure data by determining duty cycle information for a pressure pulse period at a given cuff pressure level. The duty cycle information is used to determine selected blood pressure parameters.

In still another aspect, a storage medium includes a machine readable computer program code for processing oscillometric blood pressure pulse data taken from a subject, as well as instructions for causing a computer to implement a method. The method further includes determining a pressure pulse period of a cardiac cycle of the subject, and identifying a duration of a pressure pulse detected within the pressure pulse period. A duty cycle of the pressure pulse is calculated with respect to the pressure pulse period, wherein the calculated duty cycle is used to determine selected blood pressure parameters.

In still another aspect, a computer data signal includes code configured to cause a processor to implement a method for processing oscillometric blood pressure pulse data taken from a subject. The method further includes determining a pressure pulse period of a cardiac cycle of the subject, and identifying a duration of a pressure pulse detected within the pressure pulse period. A duty cycle of the pressure pulse is calculated with respect to the pressure pulse period, wherein the calculated duty cycle is used to determine selected blood pressure parameters.

BRIEF DESCRIPTION OF DRAWINGS

Referring to the exemplary drawings wherein like elements are numbered alike in the several Figures.

DETAILED DESCRIPTION

Figure 1:
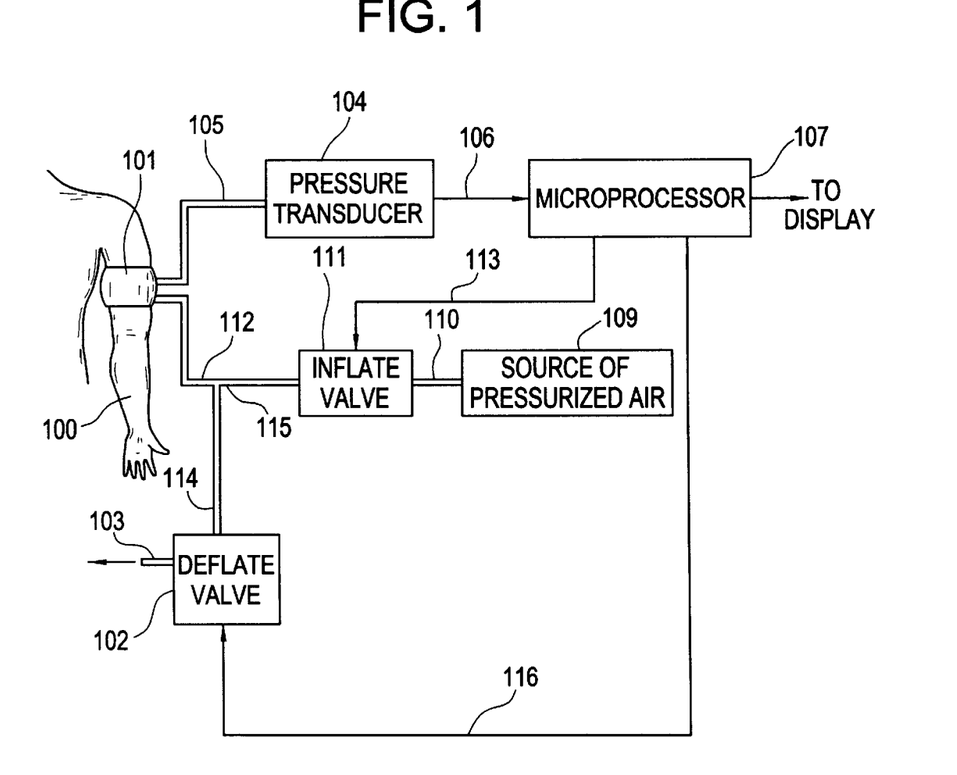
FIG. 1 is a schematic block diagram of an exemplary blood pressure measuring apparatus suitable for practicing an embodiment of the present disclosure.

Referring initially to FIG. 1, there is shown an exemplary blood pressure measuring apparatus 1 0 suitable for practicing an embodiment of the present disclosure, in which the arm 100 of a human subject is shown wearing a conventional flexible inflatable and deflatable cuff 101 for occluding the brachial artery when fully inflated. As the cuff 101 is deflated using a deflate valve 102 having exhaust 103, the arterial occlusion is gradually relieved. As will be described more fully below, the deflation of the cuff 101 via the deflate valve 102 is controlled by a microprocessor 107 through control line 116.

A pressure transducer 104 is coupled by a duct 105 to the cuff 101 for sensing the pressure therein. In a manner similar to conventional oscillometric techniques, pressure oscillations in the artery are sensed by changes in the counter-pressure of the cuff 101, with the pressure oscillations subsequently being converted into corresponding electrical signals by transducer 104 and coupled over path 106 to microprocessor 107 for processing. In addition, a source of pressurized air 109 is connected via a duct 110 through an inflate valve 111 and a duct 112 to the pressure cuff 101. The inflate valve 111 is electrically controlled through a connection 113 from the microprocessor 107. Further, the deflate valve 102 is connected by duct 114 via a branch connection 115 with the duct 112 leading to cuff 101.

During the operation of the blood pressure measuring apparatus 10, air is available at a pressure of about (for example) 8–10 p.s.i. in the source of pressurized air 109. When it is desired to initiate a determination of blood pressure, the microprocessor 107 furnishes a signal over path 113 to open the inflate valve 111, during which time the deflate valve 102 is closed. Air from the source 109 is communicated through inflate valve 111 and duct 112 to inflate the cuff 101 to a desired level, preferably above the estimated systolic pressure of the patient. Microprocessor 107 responds to a signal on path 106 from the pressure transducer 104, which is indicative of the instantaneous pressure in the cuff 101, to interrupt the inflation of the cuff 101 when the pressure in the cuff 101 reaches a predetermined value above the estimated systolic pressure of the patient. Such interruption is accomplished by sending a signal over path 113 instructing inflate valve 111 to close. Once inflate valve 111 has been closed, the blood pressure measurement can be obtained by commencing the deflate routine, during which the deflate valve 102 is operated using signal 116 from microprocessor 107.

The actual measurement of the blood pressure (under the control of the microprocessor 107 and the deflate valve 102 as sensed by pressure transducer 104) may be accomplished in any suitable manner known to those skilled in the art. At the completion of each measurement cycle, the deflate valve 102 can be re-opened long enough to relax the cuff pressure via exhaust 103. Thereafter, the deflate valve 102 is closed for the start of a new measurement cycle. As stated previously, in conventional oscillometric blood pressure monitoring, the processing of the signals from pressure transducer 104 by the microprocessor 107 is carried out in a manner so as to determine the MAP by identifying the point of maximum pulse amplitude. Typically, the cuff deflation operation is accomplished in equal decrements, such as by about 8 mm Hg per step.

Figure 2:
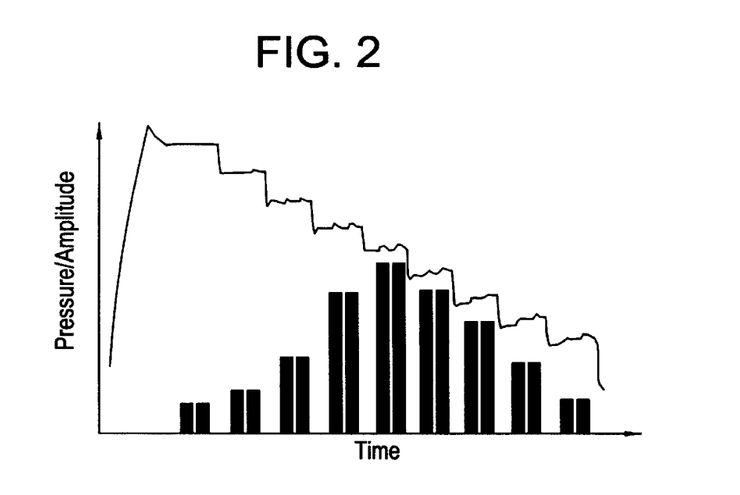
FIG. 2 is a graph illustrating conventional oscillometry data, as taken by a step deflate procedure using the apparatus of FIG. 1.

FIG. 2 is a graph illustrating conventional oscillometry data, as taken by a step deflate procedure using the apparatus 10 of FIG. 1. As the cuff pressure (solid line) is reduced from above systolic to below diastolic, the amplitude of the pulses (shaded bars, not to the same scale) varies as is shown, with the largest pulses occurring at MAP. As is also known, the microprocessor 107 may also implement programming to reject artifact data, or to analyze pulse area ratios instead of amplitude ratios. In any case, when using any of the known techniques it is preferable to determine the quality of the oscillation complexes received at each level so that the blood pressure determination is made using actual blood pressure data and not artifacts.

As described thus far, the blood pressure measuring apparatus 10 (including the signal processing software associated with microprocessor 107) operates in a conventional manner. However, in order to address the difficulties encountered by the existing amplitude-based techniques that arise from such factors as filter artifact, filter clamping and cuff pressure drift, it is desirable to modify the signal processing software to apply a new approach. Therefore, in accordance with an embodiment of the invention, there is disclosed a method for estimating blood pressure by analyzing the pressure pulse shape and determining a duty cycle thereof. The duty cycle of the pressure pulse may be used in conjunction with or in lieu of amplitude information in determining blood pressure. Because duty cycle is a temporal measurement, such a measurement is much less affected by the factors that contaminate a conventional amplitude measurement.

During oscillometric blood pressure determination, the artery is subjected to static pressures through the cuff 101. The transmural pressure is the difference between the pressures inside and outside the artery. Since blood pressure varies during the cardiac cycle, peaking maximally at systole and minimally at diastole, the transmural pressure also varies accordingly since the cuff pressure remains effectively constant during this time. Thus, at cuff pressures above the patient's systolic pressure, the transmural pressure is negative during the entire cardiac cycle. That is, the external pressure is greater than the internal pressure, meaning that the artery is fully collapsed and no blood passes. The recorded pulses are thus very small in amplitude and short in duration relative to the total pulse period.

At cuff pressures between the patient's systolic and diastolic pressures, the transmural pressure alternates between positive and negative. When positive, the artery expands as the blood pressure exceeds the occlusion pressure, thereby causing a stronger pulse to be recorded. When negative, the artery collapses, during which no pulse shape can be discerned above the steady state cuff pressure level. Therefore, a recorded pressure pulse may be partitioned into a time during which blood passes (i.e., positive transmural pressure) and a time during which the artery is collapsed (i.e., negative transmural pressure). The relative duration of the former with respect to the entire pulse period is the duty cycle, which varies from small values at near-systolic cuff pressures to about 100% at near-diastolic pressures.

Figure 3:
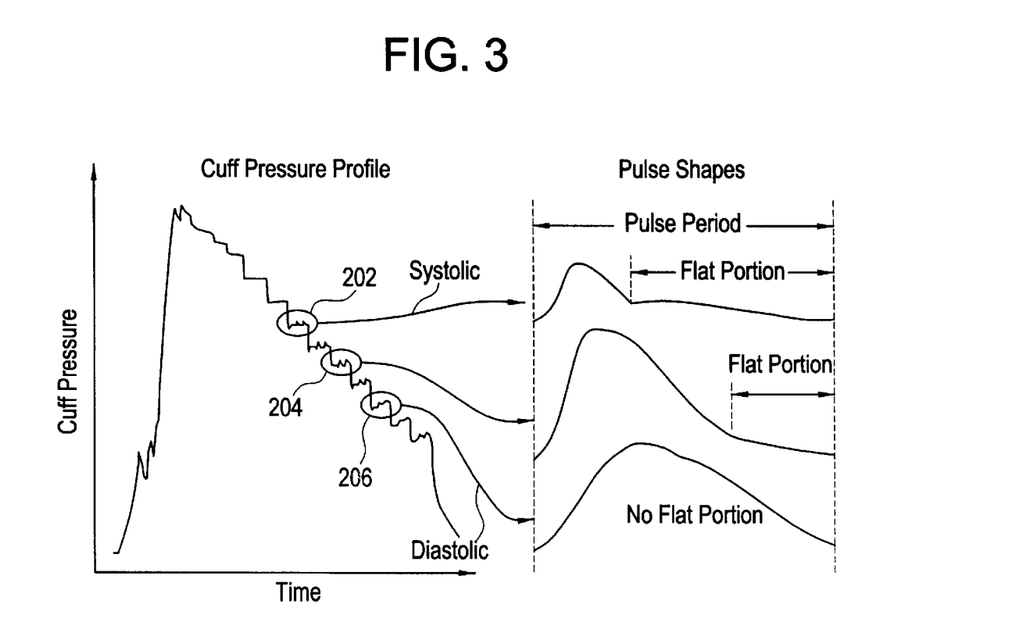
FIG. 3 is a cuff pressure profile graph illustrating recorded pulse pressure as it varies in accordance with the applied cuff pressure, and thereby duty cycle.

Referring now to FIG. 3, there is shown a cuff pressure profile graph illustrating recorded pulse pressure as it varies in accordance with the applied cuff pressure. More particularly, selected individual pulse shapes are isolated and enlarged as seen in the right portion of the figure. In selected region 202, a pulse period determined at systolic pressure includes a relatively short pulse duration and a relatively long flat portion. Accordingly, the duty cycle (defined as the duration of the pulse divided by the pulse period) is fairly low. As the applied cuff pressure lessens (selected region 204), the pulse duration becomes longer and the flat portion becomes shorter with respect to the overall pulse period. That is, the duty cycle is increased. Then, at diastolic pressure (selected region 206), the entire pulse period is encompassed by the pulse, with no flat portion. In other words, the duty cycle is then at 100%.

Figure 4:
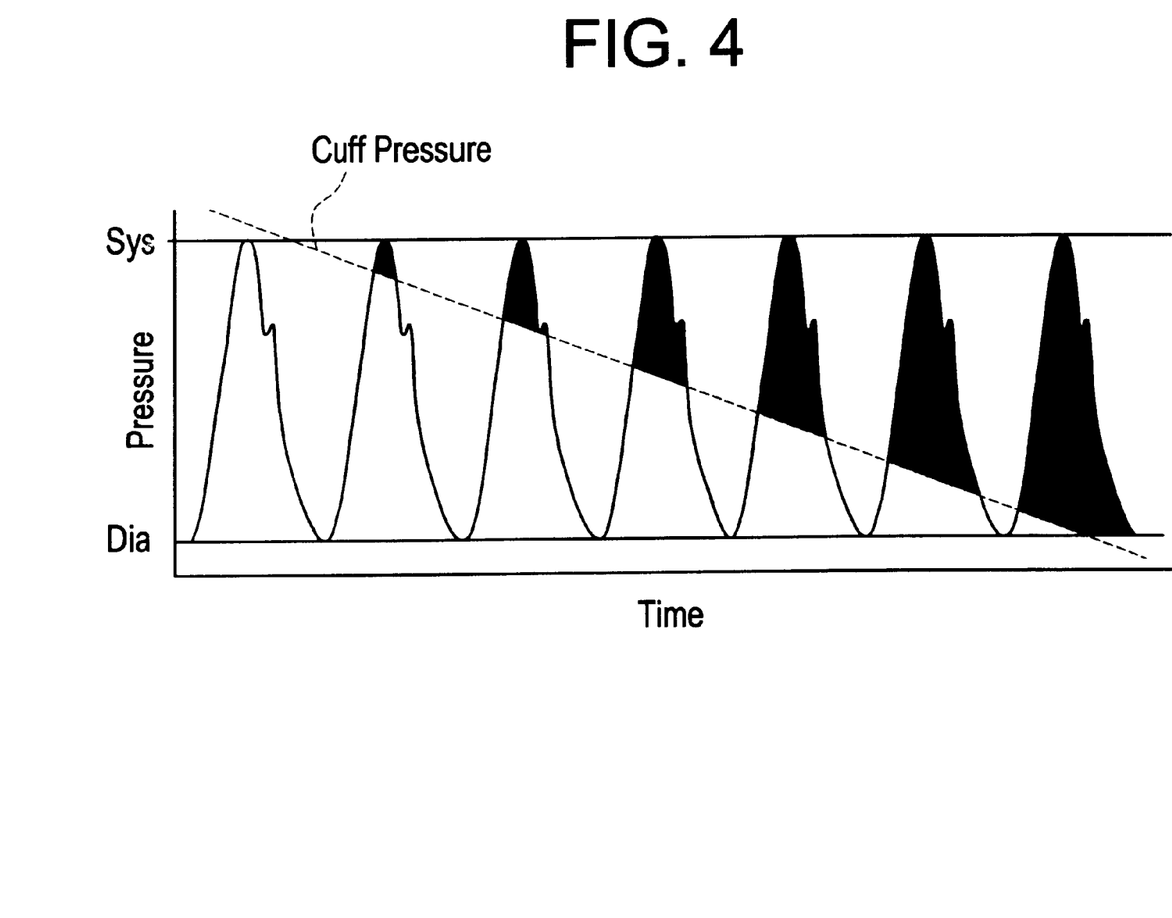
FIG. 4 is a graph of actual blood pressure versus declining cuff pressure.

Once the duty cycle for each pressure pulse at a given cuff pressure is determined, the data may then be used to identify the key blood pressure parameters. One possible approach is apply simple numerical thresholds to duty cycles, and interpolating as necessary. For example, the diastolic cuff pressure may be characterized as that cuff pressure where the duty cycle becomes 100%. Other approaches are also contemplated, however, such as using the rate of change of duty cycle with cuff pressure in identifying blood pressure parameters. Regardless of the way the parameters are defined, the use of duty cycle is time dependent, and need not depend upon pulse signal amplitude. FIG. 4 illustrates a graph of actual blood pressure versus declining cuff pressure. As can be seen, when the cuff pressure is reduced, the portion of the pulse complex exceeding the cuff pressure (shaded areas) becomes longer in duration.

Given that the pulse data collected by apparatus 10 will be analyzed in a different manner than the conventional methods, a corresponding adjustment to the software used by microprocessor 107 is implemented. More specifically, the stored digital pulse data will be analyzed to differentiate between the pulse portion and the flat portion of the pulse period. To this end, a curve fitting or template-matching algorithm may be employed to compare the pulse data with a characteristic blood pressure pulse. One such example of a suitable nonlinear curve fitting algorithm is the Levenberg-Marquardt method, which is well known to those skilled in the art. The Levenberg-Marquardt algorithm has proved to be an effective and popular way to solve nonlinear least squares problems. Software products featuring Levenberg-Marquardt routines include IMSL, MATLAB, ODRPACK and PROC NLP, among others.

Figure 5A:
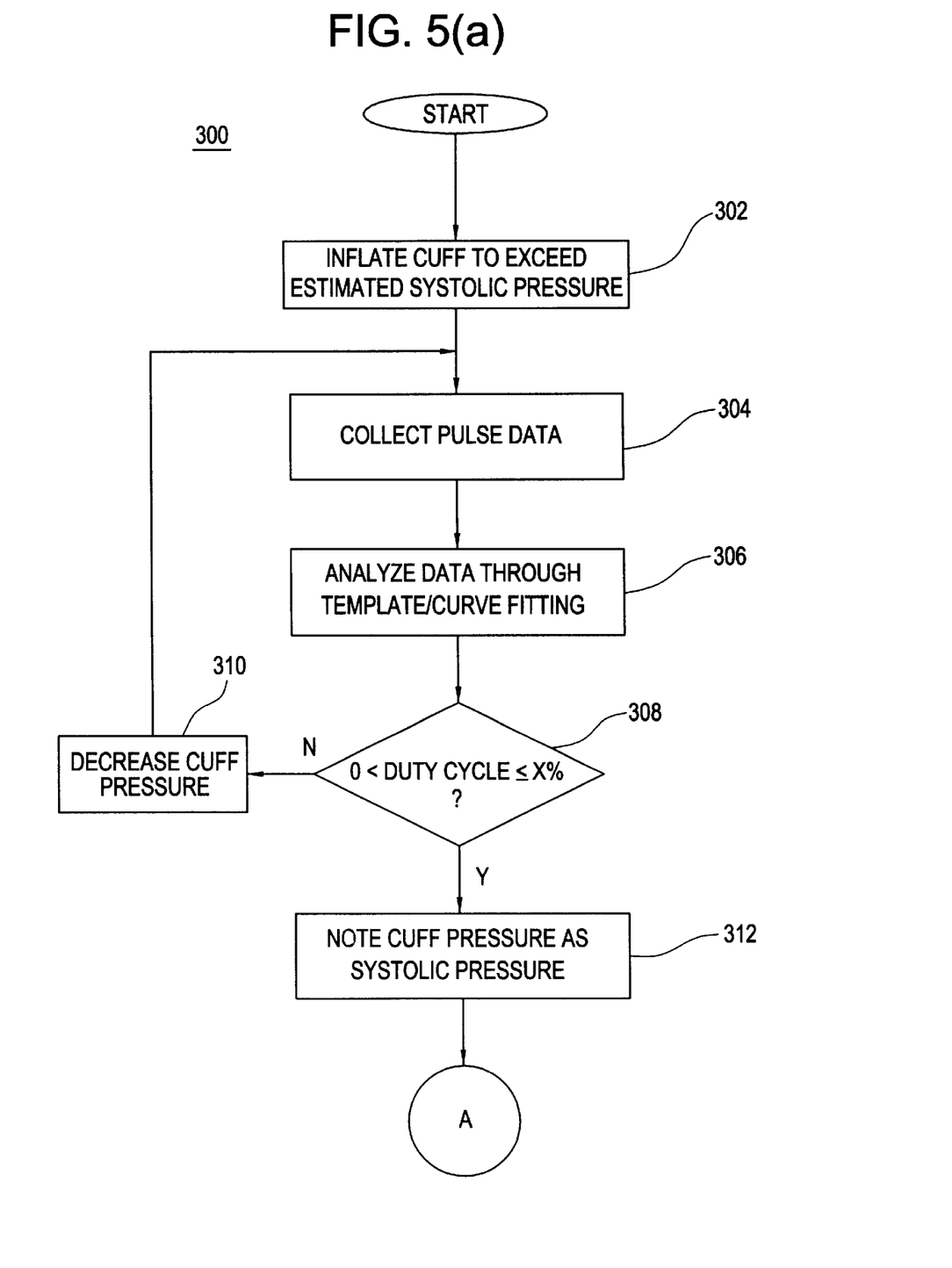
FIG. 5 is a flow diagram illustrating a method of obtaining a blood pressure measurement, in accordance with an embodiment of the invention.
Figure 5B:
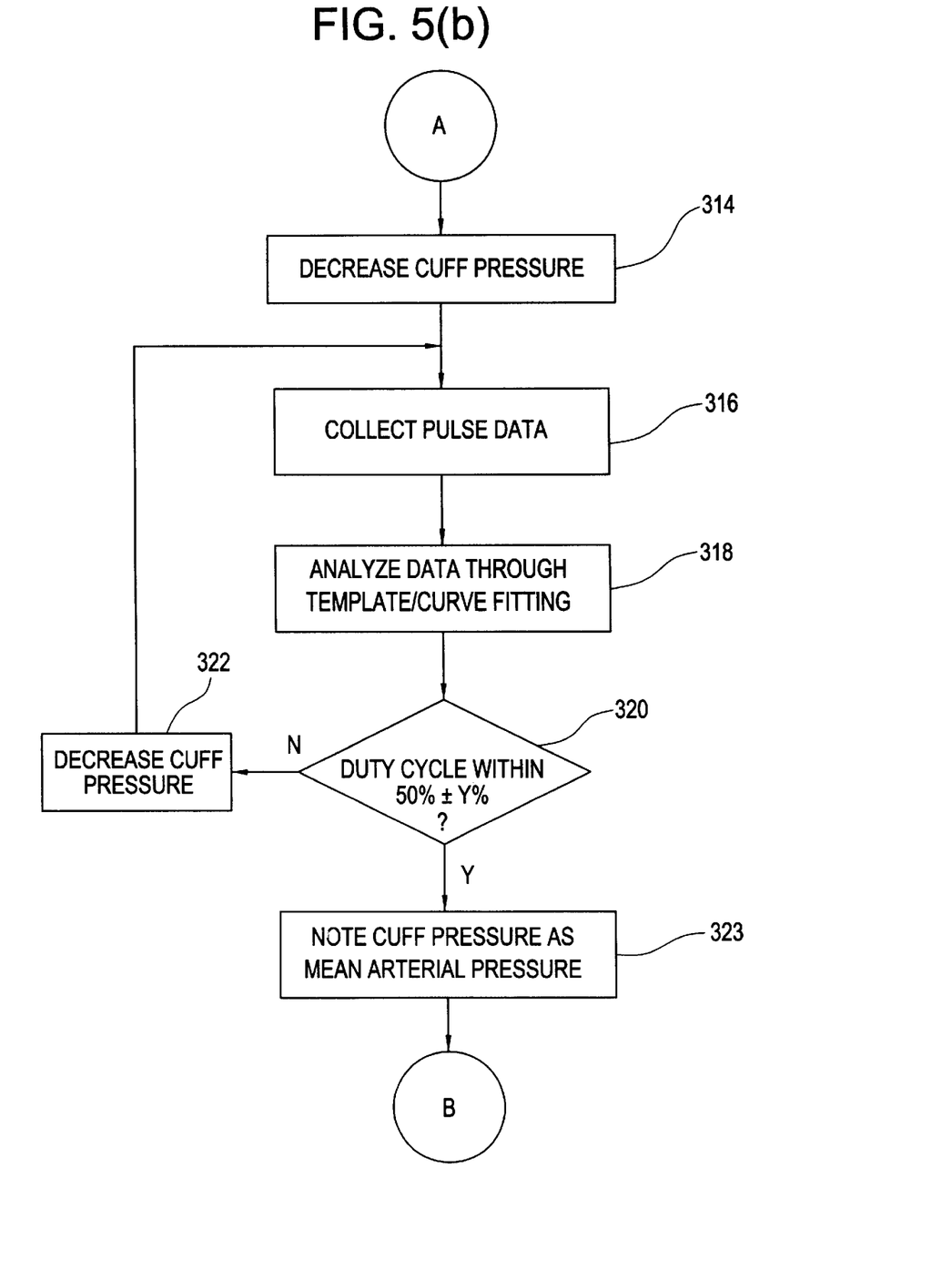
Figure 5C:
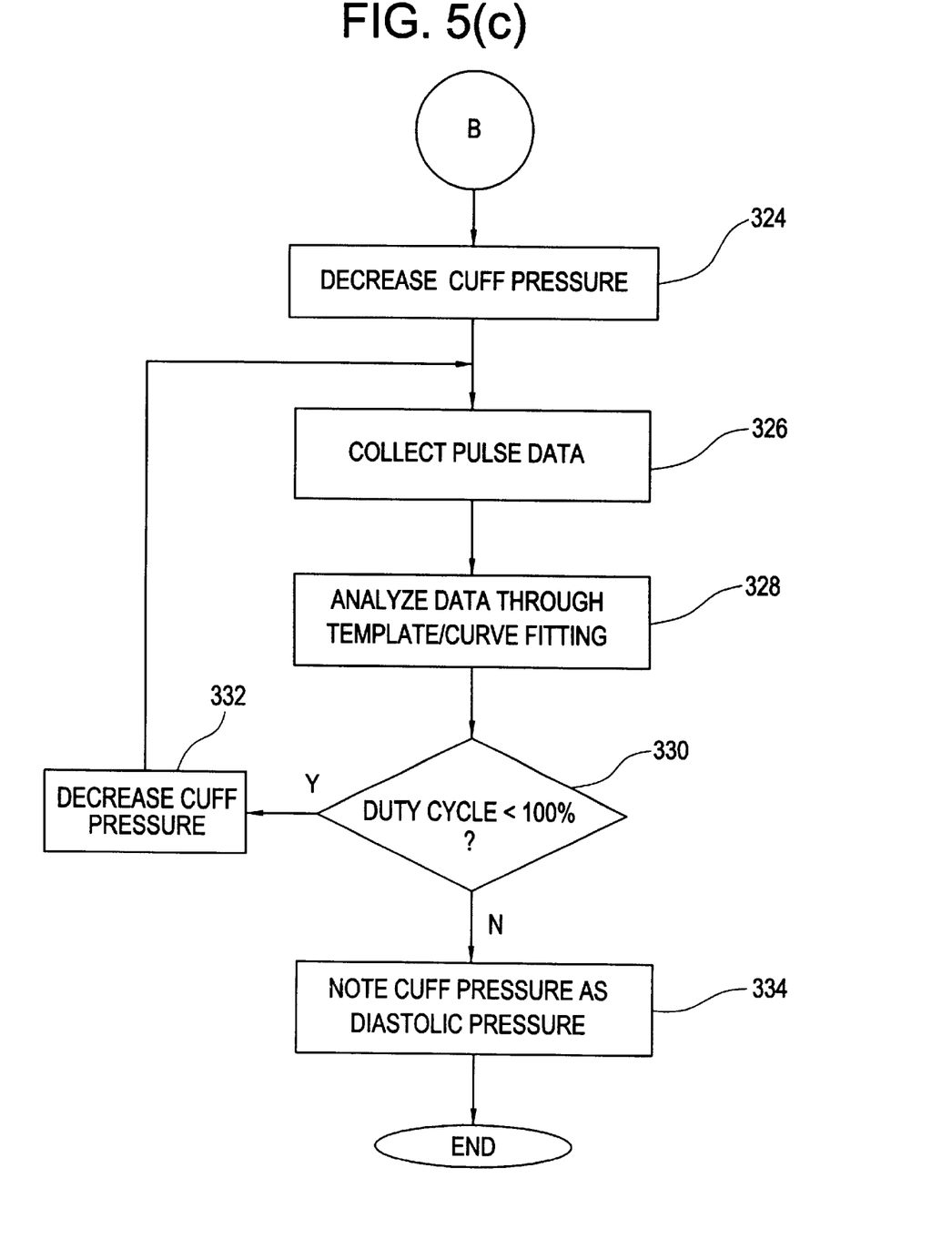

Finally, FIG. 5 is a flow diagram illustrating an exemplary method 300 of measuring the blood pressure of a subject patient through the pulse data duty cycle analysis described above. Beginning at block 302, a cuff placed around the arm of the subject is inflated to pressure exceeding an estimated systolic pressure of the patient. Once the cuff is inflated, the method 300 proceeds to block 304 where the pulse pressure data is first collected. The data is then analyzed at block 306 for duty cycle information in a manner as described above. At decision block 308, it is determined whether the duty cycle for the current pulse period is greater than zero, but less than a designated percentage (indicated as x%). This designated percentage may be determined by empirical means or otherwise so as to reflect a duty cycle representative of the systolic pressure. If the answer to decision block is "no", then the cuff pressure exceeds the systolic pressure, and the cuff pressure is decreased by a determined increment at block 310 and the method 300 returns to block 304 for further pulse data collection.

This return loop will continue (with cuff pressure continuing to be incrementally decreased) until such time as the determined duty cycle is finally within the range as specified in block 308. When the answer to decision block 308 becomes "yes", the cuff pressure at that point is registered (at block 312) as the systolic pressure of the patient. The method 300 then continues on to block 314, where the cuff pressure is further decreased. The pulse pressure data is collected at block 316 and analyzed at block 318, as was the case in determining the systolic pressure. Then, at decision block 320, it is determined whether the duty cycle is within a predetermined range of 50% (e.g., 50%±10%), thereby indicating the establishment of MAP. If not, the cuff pressure is decreased at block 322 and the method 300 is returned to block 316 for further data collection.

When the answer to decision block 320 is in the affirmative, the present cuff pressure is noted as the MAP at block 323, and the method 300 then moves to the final subprocess of determining diastolic pressure. Once again, the cuff pressure is further decreased at block 324, and the pressure pulse data is collected and analyzed at blocks 326 and 328, respectively. The inquiry at decision block 330 is concerned with whether the duty cycle is still less than about 100%. If so, the diastolic pressure has not been reached by the decreasing cuff pressure. The pressure is accordingly decreased at block 332, and the method loops back to block 324. Eventually, the pulse duty cycle will equal about 100%, at which time the cuff pressure is noted as the diastolic pressure.

In the embodiment exemplified by FIG. 5, no amplitude data need be directly considered in determining the blood pressure parameters. However, there may be instances in which the duty cycle approach is used in combination with the amplitude approach. For instance, if an initial estimate of a patient's systolic pressure is unavailable from which set an initial pump-up target pressure, an amplitude based approach may be used to re-pump partway through the determination (e.g., the patient has high blood pressure). In such a case, the duty cycle approach would make a quicker determination of the re-pump target pressure.

While the method of FIG. 5 may be used in conjunction with the apparatus in FIG. 1, it is contemplated that the method may also be used in a wide range of oscillometric devices. For example, instead of a step deflate device for providing discrete cuff pressure levels for a brief period of time, a linear deflate device may also be used.

Still another advantage of the duty cycle approach is that the measurement process may be reversed such that the cuff pressure is gradually increased from a loose fit around a patient's arm until diastolic pressure is initially detected. The pressure is then increased until the MAP is detected, and then further increased until the systolic pressure is finally detected. Once the systolic pressure is detected, there is no need to apply any further pressure, thus reducing the potential for patient discomfort.

As will be appreciated, the disclosed invention can be embodied in the form of computer or controller implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer or controller, the computer becomes an apparatus for practicing the invention. The present invention may also be embodied in the form of computer program code or signal, for example, whether stored in a storage medium, loaded into and/or executed by a computer or controller, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of processing oscillometric blood pressure pulse data taken from a subject, the method comprising:
   determining a pressure pulse period of a cardiac cycle of the subject;
   identifying a duration of a pressure pulse detected within said pressure pulse period; and
   calculating a duty cycle of said pressure pulse with respect to said pressure pulse period;
   wherein said calculated duty cycle is used to determine selected blood pressure parameters.

2. The method of claim 1, wherein said identifying a duration of a pressure pulse within said pressure pulse period is repeated over a plurality of cuff pressure levels applied to the subject.

3. The method of claim 2, further comprising:
   identifying a systolic pressure when said duty cycle is between zero and a first designated percentage.

4. The method of claim 2, further comprising:
   identifying a diastolic pressure when said duty cycle is at about 100%.

5. The method of claim 2, further comprising:
   identifying a mean arterial pressure (MAP) when said duty cycle is at about 50% plus or minus a second designated percentage.

6. The method of claim 1, wherein said identifying a duration of a pressure pulse within said pressure pulse period comprises applying a curve fitting algorithm to the pressure pulse data, thereby determining a pulse portion of said pulse period and a flat portion of said pulse period.

7. A method of measuring the blood pressure of a subject, the method comprising:
   inflating a cuff placed over an arm of the subject, thereby applying a plurality of pressure levels thereto;
   at each pressure level, obtaining pulse pressure data caused by blood pressure pulses within the arm of the subject; and
   calculating, from said pulse pressure data, a duty cycle for a pressure pulse period;
   wherein said duty cycle is used to determine selected blood pressure parameters.

8. The method of claim 7, further comprising:
   identifying a systolic pressure when said duty cycle is between zero and a first designated percentage;
   identifying a diastolic pressure when said duty cycle is at about 100%; and
   identifying a mean arterial pressure (MAP) when said duty cycle is at about 50% plus or minus a second designated percentage.

9. The method of claim 8, wherein said calculating a duty cycle from said pulse pressure data comprises identifying a duration of a pressure pulse within a pressure pulse period a pressure pulse period of a cardiac cycle of the subject by applying a curve fitting algorithm to said pressure pulse data, thereby determining a pulse portion of said pulse period and a flat portion of said pulse period.

10. The method of claim 9, wherein:
    said cuff is initially inflated to a cuff pressure greater than the estimated systolic pressure of the subject;
    said cuff pressure is gradually decreased until said systolic pressure is identified;
    said cuff pressure is further gradually decreased until said MAP is identified; and
    said cuff pressure is further gradually decreased until said diastolic pressure is identified.

11. The method of claim 9, wherein:
    said cuff is initially inflated to a cuff pressure less than the estimated diastolic pressure of the subject;
    said cuff pressure is gradually increased until said diastolic pressure is identified;
    said cuff pressure is further gradually increased until said MAP is identified; and
    said cuff pressure is further gradually increased until said systolic pressure is identified.

12. An apparatus for obtaining the blood pressure of a subject, the apparatus comprising:
    an inflatable and deflatable pressure cuff for placement around an arm of the subject;
    an inflating apparatus for inflating and pressurizing said pressure cuff;
    a deflating apparatus for selectively relieving pressure from said cuff;
    a pressure sensing device coupled to said cuff for sensing pulse pressure data caused by blood pressure pulses within the arm of the subject; and
    a microprocessor for processing said pulse pressure data by determining duty cycle information for a pressure pulse period at a given cuff pressure level;
    wherein said duty cycle information is used to determine selected blood pressure parameters.

13. The apparatus of claim 12, wherein said microprocessor determines said duty cycle information over a plurality of cuff pressure levels applied to the subject.

14. The apparatus of claim 13, wherein:
    said microprocessor identifies a systolic pressure when said duty cycle is between zero and a first designated percentage;
    said microprocessor further identifies identifying a diastolic pressure when said duty cycle is at about 100%; and said microprocessor further identifies a mean arterial pressure (MAP) when said duty cycle is at about 50% plus or minus a second designated percentage.

15. The apparatus of claim 14, wherein said microprocessor identifies a duration of a pressure pulse within said pressure pulse period by applying a curve fitting algorithm to the pressure pulse data, thereby determining a pulse portion of said pulse period and a flat portion of said pulse period.

16. The apparatus of claim 15, wherein said curve fitting algorithm is a Levenberg-Marquardt algorithm.

17. A storage medium, comprising:
a machine readable computer program code for processing oscillometric blood pressure pulse data taken from a subject; and
instructions for causing a computer to implement a method, the method further comprising:
determining a pressure pulse period of a cardiac cycle of the subject;
identifying a duration of a pressure pulse detected within said pressure pulse period; and
calculating a duty cycle of said pressure pulse with respect to said pressure pulse period;
wherein said calculated duty cycle is used to determine selected blood pressure parameters.

18. The storage medium of claim 17, wherein said identifying a duration of a pressure pulse within said pressure pulse period is repeated over a plurality of cuff pressure levels applied to the subject.

19. The storage medium of claim 18, wherein the method further comprises:
identifying a systolic pressure when said duty cycle is between zero and a first designated percentage; and
identifying a diastolic pressure when said duty cycle is at about 100%.

20. The storage medium of claim 19, wherein the method further comprises:
identifying a mean arterial pressure (MAP) when said duty cycle is at about 50% plus or minus a second designated percentage.

21. The storage medium of claim 17, wherein said identifying a duration of a pressure pulse within said pressure pulse period comprises applying a curve fitting algorithm to the pressure pulse data, thereby determining a pulse portion of said pulse period and a flat portion of said pulse period.

22. A computer data signal, comprising:
code configured to cause a processor to implement a method for processing oscillometric blood pressure pulse data taken from a subject, the method further comprising:
determining a pressure pulse period of a cardiac cycle of the subject;
identifying a duration of a pressure pulse detected within said pressure pulse period; and
calculating a duty cycle of said pressure pulse with respect to said pressure pulse period;
wherein said calculated duty cycle is used to determine selected blood pressure parameters.

23. The computer data signal of claim 22, wherein said identifying a duration of a pressure pulse within said pressure pulse period is repeated over a plurality of cuff pressure levels applied to the subject.

24. The computer data signal of claim 23, wherein the method further comprises:
identifying a systolic pressure when said duty cycle is between zero and a first designated percentage; and
identifying a diastolic pressure when said duty cycle is at about 100%.

25. The computer data signal of claim 24, wherein the method further comprises:
identifying a mean arterial pressure (MAP) when said duty cycle is at about 50% plus or minus a second designated percentage.

26. The computer data signal of claim 17, wherein said identifying a duration of a pressure pulse within said pressure pulse period comprises applying a curve fitting algorithm to the pressure pulse data, thereby determining a pulse portion of said pulse period and a flat portion of said pulse period.

* * * * *

UNITED STATES PATENT AND TRADEMARK OFFICE
CERTIFICATE OF CORRECTION

PATENT NO. : 6,767,328 B2
DATED : July 27, 2004
INVENTOR(S) : Robert Stanley Kulik It is certified that error appears in the above-identified patent and that said Letters Patent is hereby corrected as shown below:

Title page,
Item [56], References Cited, OTHER PUBLICATIONS,
"Levenber-Marquardt Method," reference, after "/Guide/" delete "OptWEb" and insert -- OptWeb --; and
"Maynard Ramsey" (2nd occurrence), after "Ramsey" delete "III2" and insert -- III --.

Column 3,
Line 23, after "apparatus" delete "1 0" and insert -- 10 --.

Column 10,
Line 6, after "signal" insert -- embodied in a carrier wave --.

Signed and Sealed this

Third Day of January, 2006

JON W. DUDAS
*Director of the United States Patent and Trademark Office*